US008207375B2

(12) United States Patent
Grass et al.

(10) Patent No.: US 8,207,375 B2
(45) Date of Patent: Jun. 26, 2012

(54) MICROPOROUS CATALYST AND METHOD FOR HYDROGENATING AROMATIC COMPOUNDS

(75) Inventors: Michael Grass, Haltern am See (DE); Alfred Kaizik, Marl (DE); Wilfried Bueschken, Haltern am See (DE); Axel Tuchlenski, Weinheim (DE); Dietrich Maschmeyer, Recklinghausen (DE); Kurt-Alfred Gaudschun, Recklinghausen (DE); Frank Brocksien, Duelmen (DE)

(73) Assignee: Evonik Oxeno GmbH, Marl (DE)

( * ) Notice: Subject to any disclaimer, the term of this patent is extended or adjusted under 35 U.S.C. 154(b) by 1179 days.

(21) Appl. No.: 12/025,292

(22) Filed: Feb. 4, 2008

(65) Prior Publication Data
US 2008/0146832 A1 Jun. 19, 2008

Related U.S. Application Data

(62) Division of application No. 10/519,413, filed as application No. PCT/EP03/06002 on Jun. 7, 2003, now abandoned.

(30) Foreign Application Priority Data

Jul. 19, 2002 (DE) .................................. 102 32 868

(51) Int. Cl.
  *C08C 19/02* (2006.01)
  *C07C 51/36* (2006.01)
  *B01J 35/10* (2006.01)

(52) U.S. Cl. ............ 562/509; 525/338; 502/80; 502/84; 502/103; 502/104; 506/127

(58) Field of Classification Search ........................ None
See application file for complete search history.

(56) References Cited

U.S. PATENT DOCUMENTS

| | | |
|---|---|---|
| 4,018,706 A | 4/1977 | Inoue et al. |
| 4,314,982 A | 2/1982 | Norman et al. |
| 4,422,960 A | 12/1983 | Shiroto et al. |
| 4,427,576 A | 1/1984 | Dupin |
| 4,517,395 A | 5/1985 | Obenaus et al. |
| 4,665,274 A | 5/1987 | Ichihashi et al. |
| 5,137,855 A | 8/1992 | Hegedus et al. |
| 5,242,880 A | 9/1993 | Irick, Jr. |
| 5,258,348 A | 11/1993 | Van Buren et al. |
| 5,558,766 A | 9/1996 | Prada et al. |
| 5,856,578 A | 1/1999 | Siegrist et al. |
| 6,284,917 B1 | 9/2001 | Brunner et al. |
| 6,344,568 B1 | 2/2002 | Okuno et al. |
| 6,743,819 B1 | 6/2004 | Manzer |
| 7,361,714 B2 | 4/2008 | Grass et al. |
| 2004/0097773 A1 | 5/2004 | Beckmann et al. |
| 2004/0260113 A1 | 12/2004 | Bueschken et al. |
| 2005/0038285 A1 | 2/2005 | Maschmeyer et al. |
| 2006/0036121 A1 | 2/2006 | Kaizik et al. |
| 2006/0041167 A1 | 2/2006 | Grass et al. |
| 2006/0167151 A1 | 7/2006 | Grass et al. |

FOREIGN PATENT DOCUMENTS

| | | |
|---|---|---|
| DE | 44 19 974 | 3/1996 |
| DE | 199 27 978 | 12/2000 |
| WO | 99/32427 | 7/1999 |
| WO | 00/78704 | 12/2000 |
| WO | 02/43862 | 6/2002 |

*Primary Examiner* — Yevegeny Valenrod
(74) *Attorney, Agent, or Firm* — Oblon, Spivak, McClelland, Maier & Neustadt, L.L.P.

(57) ABSTRACT

The invention relates to the hydrogenation of aromatic compounds, in particular the preparation of alicyclic polycarboxylic acids or their esters by core hydrogenation of the corresponding aromatic polycarboxylic acids or their esters, and also to catalysts suitable therefore.

12 Claims, No Drawings

US 8,207,375 B2

MICROPOROUS CATALYST AND METHOD FOR HYDROGENATING AROMATIC COMPOUNDS

CROSS REFERENCE TO RELATED APPLICATIONS

This application is a division of U.S. patent application Ser. No. 10/519,413, which is the U.S. national stage of International Application No. PCT/EP03/06002, filed Jun. 7, 2003, the disclosures of which are incorporated herein by reference in their entireties. This application claims priority to German Application Number 102 32 868.4, filed Jul. 19, 2002, the disclosure of which is incorporated herein by reference in its entirety.

BACKGROUND

The invention relates to the hydrogenation of aromatic compounds, in particular the preparation of alicyclic polycarboxylic acids or their esters by core hydrogenation of the corresponding aromatic polycarboxylic acids or their esters, and also to catalysts suitable therefor.

Alicyclic polycarboxylic esters, for example the esters of cyclohexane-1,2-dicarboxylic acid, are used as lubricant components and as assistants in metal processing. They also find use as plasticizers for polyolefins and for PVC.

For plasticizing PVC, esters of phthalic acid are used predominantly, for example the dibutyl, dioctyl, dinonyl or didecyl esters. Since the use of these phthalates has been discussed with increasing controversy in recent times, their use in plastics could be restricted. Alicyclic polycarboxylic esters, some of which have already been described as plasticizers for plastics in the literature, could then be available as suitable substitutes.

In most cases, the most economical route for preparing alicyclic polycarboxylic esters is the core hydrogenation of the corresponding aromatic polycarboxylic esters, for example the abovementioned phthalates. Some, processes already exist for this purpose:

U.S. Pat. No. 5,286,898 and U.S. Pat. No. 5,319,129 describe processes with which dimethyl terephthalate may be hydrogenated over supported Pd catalysts which are doped with Ni, Pt and/or Ru at temperatures greater than or equal to 140° C. and a pressure between 50 and 170 bar to give the corresponding dimethyl hexahydroterephthalate.

U.S. Pat. No. 3,027,398 discloses the hydrogenation of dimethyl terephthalate over supported Ru catalysts at from 110 to 140° C. and from 35 to 105 bar.

DE 28 23 165 discloses the hydrogenation of aromatic carboxylic esters over supported N1, Ru, Rh and/or Pd catalysts to the corresponding alicyclic carboxylic esters at from 70 to 250° C. and from 30 to 200 bar. A macroporous support having an average pore size of 70 nm and a BET surface area of approx. 30 m$^2$/g is used.

WO 99/32427 and WO 00/78704 disclose processes for hydrogenating benzenepolycarboxylic esters to the corresponding alicyclic compounds. Supported catalysts are used which comprise a metal of transition group, VIII alone or together with at least one metal of transition group I or VII of the Periodic Table and have macropores. A preferred metal of transition group VIII used is ruthenium. To hydrogenate, three different catalyst types are used which differ substantially by their average pore diameter and BET surface areas.

Catalyst I: average pore. diameter greater than 50 nm and BET surface area less than 30 m$^2$/g Catalyst II: average pore diameter from 5 to 20 nm and BET surface area greater than 50 m$^2$/g Catalyst III: average-pore diameter greater than 100 nm and BET surface area less than 15 m$^2$/g In addition to the pore diameter, the pore volume formed by pores of a certain diameter is specified. The support materials used in the preparation of catalyst II have a pore distribution in which from approx. 5 to approx. 50% of the pore volume by macropores (diameter from approx. 50 nm to 10 000 nm) and from approx. 70 to approx. 90% of the pore volume by mesopores (diameter from approx. 2 to 50 nm). The average pore diameter is between approx. 5 and 20 nm.

The activity and selectivity of hydrogenation catalysts depends on their surface properties such as pore size, BET surface area or surface concentration of the active metals.

The catalysts used for the core hydrogenation of aromatic carboxylic acids or their esters should allow a high reaction rate, only generate a small proportion of by-products and have a long on-stream time.

In a continuously operated process, a catalyst is exposed to mechanical, thermal and chemical stresses which change the pore size and the BET surface area and thus reduce the activity and selectivity of this catalyst.

In addition to mechanical abrasion, many catalysts also exhibit an expansion of the pore volumes and diameter due to acid digestion.

Aromatic polycarboxylic esters frequently contain small amounts of carboxylic acids, and traces of acid additionally form during the core hydrogenation of esters. Partial esters of polycarboxylic acids or polycarboxylic acids themselves are acidic as a consequence of their structure. Therefore, a hydrogenation catalyst suitable for a continuous process should be resistant to acid even at relatively high temperatures under the hydrogenation conditions.

The surface properties of the catalysts are also responsible for their reactivity. The existing catalysts are in need of improvement in this respect.

SUMMARY

It has now been found that, surprisingly, catalysts which comprise at least one metal of the eighth transition group of the Periodic Table and consist of a support material having an average pore diameter of from 2 to 50 nm and a narrow pore distribution having a fine-pored surface structure hydrogenate aromatic carboxylic acids and/or their esters (full or partial esters) in high selectivity and space-time yield without significant side reactions to the corresponding alicyclic polycarboxylic acids or their esters.

The present invention therefore provides a catalyst for hydrogenating aromatic compounds to the corresponding alicyclic compounds, said catalyst comprising at least one metal of the eighth transition group of the Periodic Table on or in a support material, wherein the support material has an average pore diameter of from 2 to 50 nm and that over 91% of the total pore volume of the support materials is accounted for by pores having a diameter of less than 50 nm.

Catalysts of this type may be used particularly for hydrogenating aromatic compounds. A process for catalytically hydrogenating aromatic compounds using hydrogen-containing gases over a catalyst which comprises at least one metal of the eighth transition group of the Periodic Table on or in a support material, wherein that the support material has an average pore diameter of from 2 to 50 nm and over 91% of the total pore volume of the support materials is accounted for by pores having a diameter of less than 50 nm likewise forms part of the subject matter of the present invention.

DETAILED DESCRIPTION OF EXEMPLARY EMBODIMENTS

In principle, the catalysts may comprise any metal of the eighth transition group of the Periodic Table. The active metals used are preferably platinum, rhodium, palladium, cobalt, nickel or ruthenium or a mixture of two or more thereof, and ruthenium in particular is used as the active metal.

In addition to the metals already mentioned, at least one metal of the first and/or seventh transition group of the Periodic Table may additionally be present in the catalysts. Preference is given to using rhenium and/or copper.

The content of active metals, i.e. the metals of the first and/or seventh and/or eighth transition group of the Periodic Table is generally from 0.1 to 30% by mass. The noble metal content, i.e. the metals of the eighth transition group of the Periodic Table and of the fifth or sixth period, e.g. palladium, ruthenium, calculated as the metal, is in the range from 0.1 to 10% by mass, in particular in the range from 0.8 to 5% by mass, very particularly between 1 and 3% by mass.

To prepare the catalysts according to the invention, support materials having an average pore diameter which is in the range from 2 to 50 nm are used. (The average pore diameter is determined by Hg porosimetry, in particular to DIN 66133.)

In the case of the support materials used, it is possible to distinguish between micropores (pore diameter less than 2 nm), mesopores (pore diameter from 2 to 50 nm) and macropores (pore diameter greater than 50 nm). With regard to the pore type, support materials having the following pore combinations can be used:
 a) only mesopores
 b) micropores and mesopores
 c) mesopores and macropores
 d) micropores and mesopores and macropores
 e) micropores and macropores It is decisive for the preparation of the catalysts according to the invention that, irrespective of the pore size distribution, the average pore diameter of the support material is between 2 and 50 nm. Preferably, the average pore diameter is from 5 to 24 nm, more preferably from 10 to 19 nm.

The specific surface area of the support (determined by the BET process by nitrogen adsorption, to DIN 66 131 is 1-350 $m^2/g$, preferably 1-200 $m^2/g$, more preferably 1-100 $m^2/g$, in particular 10-90 $m^2/g$ or 50-80 $m^2/g$ or 1-40 $m^2/g$.

In a specific embodiment of the invention, the catalysts are prepared using support materials in which over 95%, in particular over 97%, of the total pore volume is accounted for by micro- and mesopores, i.e. pores having a diameter of from 2 to 50 nm.

The total pore volume of the catalyst according to the invention is from 0.25 to 0.50 ml/g, in particular from 0.28 to 0.43 ml/g.

The carriers used for the preparation of the catalysts according to the invention are solids whose average pore diameter and whose specific surface area are within the abovementioned ranges. The carriers used may be, for example, the following materials: activated carbon, silicon carbide, aluminum oxide, silicon oxide, aluminosilicate, titanium dioxide, zirconium dioxide, magnesium oxide and/or zinc oxide or their mixtures. In addition, these support materials may comprise alkali metals, alkaline earth metals and/or sulfur.

The starting material used for the preparation of the catalysts according to the invention is preferably a titanium hydroxide (metatitanic acid). Metatitanic acid is obtained as an intermediate in $TiO_2$ preparation according to the classical sulfate process by digestion of ilmenite with sulfuric acid (cf. Ullmann's Encyklopadie der technischen Chemie, 4th edition, vol. 18 (1979), p. 574 ff).

The sulfuric acid-containing metatitanic acid, after substantial removal of the sulfuric acid and washing with demineralized water and also partial peptizing with nitric acid, is converted to a titanium dioxide of the anatase type by calcining at from 490 to 530° C.

The sulfuric acid may be removed by neutralizing with ammonia or alkali metal hydroxide solutions and subsequent water washing. Another possibility of deacidification involves washing the sulfuric acid-containing metatitanic acid with water-soluble barium salts, for example barium nitrate, barium chloride or barium carbonate, and washing with water. In this case, titanium dioxide is obtained which comprises barium salts and possibly small amounts of sulfuric acid and sulfate.

The material obtained in this way is ground to the desired particle sizes and sieved. The calcined $TiO_2$ powder and/or $TiO_2$ powder mixtures are homogenized with the addition of water and plasticizing assistant in a mixing apparatus, for example in a kneader or stirrer, and shaped in a shaping apparatus, for example in an extruder or a tableting machine, to give shaped bodies of a desired shape, such as extrudates or tablets. Subsequent drying at 80-120° C. and calcining at 450-550° C. provides the finished $TiO_2$ support having the pore structure according to the invention. For the improvement of the mechanical stability of the $TiO_2$ support, it is advantageous, as described in DE 44 19 974, to use a $TiO_2$ powder mixture of at least two powders of different particle size distribution for the support preparation.

In the case of the titanium dioxide supports which have been modified with barium salts and are used with preference, the barium content is between 1.0 and 4.0% by mass. The content of "free" sulfate may be 1.0-5.5% by mass. Free sulfate refers to sulfur, calculated as sulfate of oxidation state 6, which is not present as barium sulfate. Free sulfate may be determined, for example, by titration after oxidative treatment of the catalyst material in aqueous solution, since barium sulfate as a very substantially insoluble salt is not included in the determination.

The catalysts according to the invention may be obtained by applying at least one metal of the eighth transition group of the Periodic Table and optionally at least one metal of the first and/or seventh transition group of the Periodic Table to a suitable support. It is also possible to prepare the active metals and the support at the same time, i.e. use an unsupported catalyst.

The application may be achieved by saturating the support in aqueous metal solutions, for example aqueous ruthenium salt solutions, by spraying appropriate metal salt solutions onto the support or by other suitable processes. Useful metal salts of the first, seventh or eighth transition group of the Periodic Table include the nitrates, nitrosyl nitrates, halides, carbonates, carboxylates, acetylacetonates, chloro complexes, nitrito complexes or amine complexes of the appropriate metals, and preference is given to the nitrates and nitrosyl nitrates.

In the case of catalysts which, in addition to the metal of the eighth transition group of the Periodic Table, comprise further applied metals as active metals, the metal salts or metal salt solutions may be applied at the same time or in succession.

The supports coated or saturated with metal salt solution are then dried, preferably at temperatures of from 80 to 150°

C., and optionally calcined at temperatures of from 200 to 600° C. In the case of separate saturation, the catalyst is dried after each saturation step and optionally calcined as described above. The sequence in which the active components are applied can be chosen freely.

Optionally, the application of the active components, drying and calcining may be effected in one operation, for example by spraying an aqueous metal salt solution onto the support at temperatures over 200° C.

The catalysts according to the invention are advantageously brought into a shape which offers a low flow resistance on hydrogenation, for example tablets, cylinders, extrudates or rings. The shaping may be effected when desired at different points in the catalyst preparation.

In the process according to the invention, the hydrogenation is, carried out in the liquid phase or in the gas phase. The hydrogenation may be carried out continuously or batchwise over suspended catalysts or catalysts arranged in pieces in a fixed bed. In the process according to the invention, preference is given to a continuous hydrogenation over a catalyst arranged in a fixed bed in which the product/reactant phase is mainly in the liquid state under the reaction conditions.

When the hydrogenation is carried out continuously over a catalyst arranged in a fixed bed, it is advantageous to convert the catalyst into the active form before the hydrogenation. This may be affected by reducing the catalyst with hydrogen-containing gases by a temperature program. The reduction may optionally be carried out in the presence of a liquid phase which trickles over the catalyst. The liquid phase used may be a solvent or the hydrogenation product.

For the process according to the invention, different process variants may be selected. It may be carried out adiabatically, polytropically or virtually isothermally, i.e. with a temperature rise of typically less than 10° C., in one or more stages. In the latter case, all reactors, advantageously tubular reactors, may be operated adiabatically or virtually isothermally, or else one or more may be operated adiabatically and the others virtually isothermally. It is also possible to hydrogenate the aromatic compounds in straight pass or with product recycling.

Preference is given to carrying out the process according to the invention in the mixed liquid/gas phase or the liquid phase in three-phase reactors in cocurrent, and to the hydrogenating gas being distributed in the liquid reactant/product stream in a manner known per se. In the interest of uniform liquid distribution, improved removal of heat of reaction and a high space-time yield, the reactors are preferably operated with high liquid superficial velocities of from 15 to 120, in particular from 25 to 80, m$^3$ per m$^2$ of cross section of the empty reactor and hour. When a reactor is operated in straight pass, the liquid hourly space velocity (LHSV) may assume values between 0.1 and 10 h$^{-1}$.

The hydrogenation may be carried out in the absence or preferably in the presence of a solvent. Useful solvents are any liquids which form a homogeneous solution with the reactant and product, behave inertly under the hydrogenation conditions and can be easily removed from the product. The solvent may also be a mixture of several solvents and optionally comprise water.

For example, the following substances may be used as solvents:
straight-chain or cyclic ethers, for example tetrahydrofuran or dioxane, and also aliphatic alcohols in which the alkyl radical has from 1 to 13 carbon atoms.

Alcohols which can be used with preference are isopropanol, n-butanol, isobutanol, n-pentanol, 2-ethylhexanol, nonanols, technical nonanol mixtures, decanol, technical decanol mixtures and tridecanols.

When alcohols are used as solvents, it may be advantageous to use that alcohol or that alcohol mixture which would be formed on hydrolysis of the product. This would rule out by-product formation by transesterification. A further preferred solvent is the hydrogenation product itself.

The use of a solvent allows the aromatic concentration in the reactor feed to be limited, which allows better temperature control in the reactor. This may have the consequence of minimizing secondary reactions and thus increasing the product yield. The aromatic content in the reactor feed is preferably between 1 and 35%, in particular between 5 and 25%. In the case of reactors which are operated by a loop method, the desired concentration range may be attained via the circulation ratio (ratio of recycled hydrogenation effluent to reactant).

The process according to the invention is carried out within a pressure range of from 3 to 300 bar, in particular between 15 and 200 bar, very particularly between 50 and 200 bar. The hydrogenation temperatures are between 50 and 250° C., in particular between 100 and 200° C.

The hydrogenating gases used may be any desired hydrogen-containing gas mixtures which do not contain any damaging amounts of catalyst poisons, for example carbon monoxide or hydrogen sulfide. The use of inert gases is optional, and preference is given to using hydrogen in a purity of greater than 95%, in particular greater than 98%. Inert gas constituents may be, for example, nitrogen or methane.

The individual reactors may be charged with fresh hydrogen. However, in order to minimize the hydrogen consumption and the effluent losses resulting from the offgas, it is advantageous to use the offgas of one reactor as the hydrogenation gas in another reactor. For example, in a process which is carried out in two reactors connected in series, it is advantageous to feed fresh hydrogen into the second reactor and to pass the offgas of the second reactor into the first reactor. In this case, feedstock and hydrogenation gas flow in opposite sequence through the reactors. It is advantageous to maintain the hydrogen excess, based on the stoichiometric amount required, below 30%, in particular below 10%, very particularly below 5%.

When octyl or nonyl phthalates or their mixtures are converted to the corresponding 1,2-cyclohexanedicarboxylic esters, preference is given to carrying out the hydrogenation in the mixed liquid/gas or liquid phase in two reactors connected in series. The first reactor is operated in the loop method, i.e. a portion of the hydrogenation effluent of the first reactor together with fresh reactant is passed into the top of the first reactor. The other portion of the effluent of the first reactor is hydrogenated in straight pass in a second reactor. Instead of one large loop reactor, it is also possible to use a plurality of smaller loop reactors which are arranged in series or in parallel. It is likewise possible, instead of a large reactor which is flowed through in straight pass, to operate a plurality of reactors which are connected to each other in series or in parallel. However, preference is given to using only one loop reactor and only one reactor which is operated in straight pass. In the process according to the invention, the hydrogenation of octyl, nonyl, decyl or dodecyl phthalates is preferably carried out under the following conditions:

The concentration of these phthalates at the entrance of the first reactor (loop reactor) is between 1 and 30% by mass, preferably between 2 and 10% by mass, most preferably between 3 and 8% by mass. In the hydrogenation effluent of the first reactor, the concentration of the phthalates is between 0.5 and 20% by mass, in particular between 1 and 10% by mass.

The liquid hourly space velocity (LHSV, liters of fresh reactant per liter of catalyst per hour) in the loop reactor is from 0.1 to 5 $h^{-1}$, in particular from 0.5 to 3 $h^{-1}$.

The superficial velocity in the loop reactor is in the range from 10 to 100 $m^3/m^2/h$, preferably in the range from 20 to 80 $m^3/m^2/h$, most preferably in the range from 40 to 60 $m^3/m^2/h$.

The average hydrogenation temperatures in the loop reactor are from 60 to 150° C., in particular from 70 to 120° C.

The hydrogenation pressure in the loop reactor is from 25 to 200 bar, in particular from 80 to 110 bar.

In the effluent of the second reactor, the concentration of reactant is less than 0.3% by mass, in particular less than 0.1% by mass, very particularly less than 0.05% by mass.

The liquid hourly space velocity in the second reactor (liters of nonyl phthalate per liter of catalyst per hour) is from 1 to 20 $h^{-1}$, in particular from 2 to 10 $h^{-1}$.

In the second reactor, the average temperature is between 60 and 150° C., in particular 70 and 120° C.

The hydrogenation pressure in the second reactor is from 25 to 200 bar, in particular from 80 to 110 bar.

The process according to the invention allows aromatic compounds such as aromatic poly- and/or monocarboxylic acids or their derivatives, in particular their alkyl esters, to be converted to the corresponding alicyclic polycarboxylic acid compounds. Both full esters and partial esters may be hydrogenated. A full ester is a compound in which all acid groups are esterified. Partial esters are compounds having at least one free acid group (or optionally an anhydride group) and at least one ester group.

When polycarboxylic esters are used in the process according to the invention, these preferably contain 2, 3 or 4 ester functions.

The aromatic compounds or polycarboxylic esters used in the process according to the invention are preferably polycarboxylic acids of benzene, diphenyl, naphthalene and/or anthracene, their anhydrides and/or the corresponding esters. The resulting alicyclic polycarboxylic acids or their derivatives consist of one or more $C_6$ rings, optionally linked via a C—C bond or fused on.

The alcohol component of the carboxylic esters used preferably consists of branched or unbranched alkyl, cycloalkyl, or alkoxyalkyl groups having from 1 to 25 carbon atoms. These may be identical or different within one molecule of a polycarboxylic ester, i.e. they may be identical or different isomers or possess an identical or different number of carbon atoms. It will be appreciated that it is also possible to use isomers with regard to the substitution pattern of the aromatic system in the form of a mixture, for example a mixture of phthalic ester and terephthalic ester.

In a preferred embodiment, the present invention relates to a process for hydrogenating benzene-1,2-, -1,3-, or -1,4-dicarboxylic esters, and/or benzene-1,2,3-, -1,2,4-, or -1,3,5-tricarboxylic esters, i.e. the isomers of cyclohexane-1,2-, -1,3-, or -1,4-dicarboxylic esters, or of cyclohexane-1,2,3-, -1,3,5-, or -1,2,4-tricarboxylic esters are obtained.

Esters of the following aromatic carboxylic acids, for example, may be used in the process of the invention: naphthalene-1,2-dicarboxylic acid, naphthalene-1,3-dicarboxylic acid, naphthalene-1,4-dicarboxylic acid, naphthalene-1,5-dicarboxylic acid, naphthalene-1,6-dicarboxylic acid, naphthalene-1,7-dicarboxylic acid, naphthalene-1,8-dicarboxylic acid, phthalic acid (benzene-1,2-dicarboxylic acid), isophthalic acid (benzene-1,3-dicarboxylic acid), terephthalic acid. (benzene-1,4-dicarboxylic acid), benzene-1,2,3-tricarboxylic acid, benzene-1,2,4-tricarboxylic acid (trimellitic acid), benzene-1,3,5-tricarboxylic acid (trimesic acid) or benzene-1,2,3,4-tetracarboxylic acid. It is also possible to use acids which are produced from the acids mentioned by substituting one or more of the hydrogen atoms bonded to the aromatic core with alkyl, cycloalkyl, or alkoxyalkyl groups.

It is possible to use alkyl, cycloalkyl, or else alkoxyalkyl esters, for example, of the abovementioned acids, these radicals each independently including from 1 to 25, in particular from 3 to 15, very particularly from 8 to 13, particularly 9, carbon atoms. These radicals may be linear or branched. If a starting material has more than one ester group, these radicals may be identical or different.

Examples of compounds which may be used in the process of the invention as esters of an aromatic polycarboxylic acid are the following: monomethyl terephthalate, dimethyl terephthalate, diethyl terephthalate, di-n-propyl terephthalate, dibutyl terephthalate, diisobutyl terephthalate, di-tert-butyl terephthalate, monoglycol terephthalate, diglycol terephthalate, n-octyl terephthalate, diisooctyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, ditridecyl terephthalate, di-n-octadecyl terephthalate, diisooctadecyl terephthalate, di-n-eicosyl terephthalate, monocyclohexyl terephthalate; monomethyl phthalate, dimethyl phthalate, di-n-propyl phthalate, di-n-butyl phthalate, diisobutyl phthalate, di-tert-butyl phthalate, monoglycol phthalate, diglycol phthalate, di-n-octyl phthalate, diisooctyl phthalate, di-2-ethylhexyl phthalate, di-n-nonyl phthalate, diisononyl phthalate, di-n-decyl phthalate, di-2-propylheptyl phthalate, diisodecyl phthalate, di-n-undecyl phthalate, diisoundecyl phthalate, ditridecyl phthalate, di-n-octadecyl phthalate, diisooctadecyl phthalate, di-n-eicosyl phthalate, monocyclohexyl phthalate, dicyclohexyl phthalate, monomethyl isophthalate, dimethyl isophthalate, dimethyl isophthalate, diethyl isophthalate, di-n-propyl isophthalate, di-n-butyl isophthalate, diisobutyl isophthalate, di-tert-butyl isophthalate, monoglycol isophthalate, diglycol isophthalate, di-n-octyl isophthalate, diisooctyl isophthalate, 2-ethylhexyl isophthalate, di-n-nonyl isophthalate, diisononyl, isophthalate, di-n-decyl isophthalate, diisodecyl isophthalate, di-n-undecyl isophthalate, diisododecyl isophthalate, di-n-dodecyl isophthalate, ditridecyl isophthalate, di-n-octadecyl isophthalate, diisooctadecyl isophthalate, di-n-eicosyl isophthalate, monocyclohexyl isophthalate.

The process according to the invention can in principle also be applied to benzoic acid and its esters. These include benzoates of diols, for example glycol dibenzoate, diethylene glycol benzoate, triethylene glycol dibenzoate and propylene glycol dibenzoate, and also alkyl benzoates. The alcohol component of the alkyl benzoates may consist of from 1 to 25, preferably from 8 to 13, carbon atom(s). The alcohols may be linear or branched.

It is also possible to use mixtures of two or more polycarboxylic esters. Examples of such mixtures may be obtained in the following ways:

a) A polycarboxylic acid is partially esterified using an alcohol in such a way as to give both full and partial esters.

b) A mixture of at least two polycarboxylic acids is esterified using an alcohol, producing a mixture of at least two full esters.

c) A polycarboxylic acid is treated with an alcohol mixture, and the product may be a mixture of full esters.

d) A polycarboxylic acid is partially esterified using an alcohol mixture.

e) A mixture of at least two carboxylic acids is partially esterified using an alcohol mixture.

f) A mixture of at least two polycarboxylic acids is partially esterified using an alcohol mixture.

Instead of the polycarboxylic acids in reactions a) to f), their anhydrides may also be used.

Aromatic esters are frequently prepared industrially from alcohol mixtures, in particular the full esters by route c).

Examples of corresponding alcohol mixtures include:

$C_5$ alcohol mixtures prepared from linear butenes by hydroformylation followed by hydrogenation;

$C_5$ alcohol mixtures prepared from butene mixtures which comprise linear butene and isobutene, by hydroformylation followed by hydrogenation;

$C_6$ alcohol mixtures prepared from a pentene or from a mixture of two or more pentenes, by hydroformylation followed by hydrogenation;

$C_7$ alcohol mixtures prepared from triethylene or dipropene or from a hexene isomer or from another mixture of hexene isomers, by hydroformylation followed by hydrogenation;

$C_8$ alcohol mixtures, such as 2-ethylhexanol (2 isomers), prepared by aldol condensation of n-butyraldehyde followed by hydrogenation;

$C_9$ alcohol mixtures prepared from $C_4$ olefins by dimerization, hydroformylation, and hydrogenation. The starting materials for preparing the $C_9$ alcohols may be isobutene or a mixture of linear butenes or mixtures of linear butenes and isobutene. The $C_4$ olefins may be dimerized with the aid of various catalysts, for example protic acids, zeolites, organometallic nickel compounds, or solid nickel catalysts. The $C_8$ olefin mixtures may be hydroformylated with the aid of rhodium catalysts or cobalt catalysts. There is therefore a wide variety of industrial $C_9$ alcohol mixtures.

$C_{10}$ alcohol mixtures prepared from tripropylene by hydroformylation followed by hydrogenation; 2-propylheptanol (2 isomers) prepared by aldol condensation of valeraldehyde followed by hydrogenation;

$C_{10}$ alcohol mixtures prepared from a mixture of at least two $C_5$ aldehydes by aldol condensation followed by hydrogenation;

$C_{13}$ alcohol mixtures prepared from hexaethylene, tetrapropylene, or tributene, by hydroformylation followed by hydrogenation.

Other alcohol mixtures may be obtained by hydroformylation followed by hydrogenation from olefins or olefin mixtures which arise, for example, in Fischer-Tropsch syntheses, in dehydrogenations of hydrocarbons, in metathesis reactions, in the polygas process, or in other industrial processes.

Olefin mixtures with olefins of differing carbon numbers may also be used to prepare alcohol mixtures.

In the process of the invention, any ester mixture prepared from aromatic polycarboxylic acids and the abovementioned alcohol mixtures may be used. According to the invention, preference is given to esters prepared from phthalic acid or phthalic anhydride and a mixture of isomeric alcohols having from 6 to 13 carbon atoms.

Examples of industrial phthalates which can be used in the process of the invention include products with the following trade names:

Vestinol C (di-n-butyl phthalate) (CAS No. 84-74-2); Vestinol IB (diisobutyl phthalate) (CAS No. 84-69-5); Jayflex DINP (CAS No. 68515-48-0); Jayflex DIDP (CAS No. 68515-49-1); Palatinol 9P (68515-45-7), Vestinol 9 (CAS No. 28553-12-0); TOTM (CAS No. 3319-31-1); Linplast 68-TM, Palatinol N (CAS No. 28553-12-0); Jayflex DHP (CAS No. 68515-50-4); Jayflex DIOP (CAS No. 27554-26-3); Jayflex UDP (CAS. No. 68515-47-9); Jayflex DIUP (CAS No. 85507-79-5); Jayflex DTDP (CAS No. 68515-47-9); Jayflex L9P (CAS NO. 68515-45-7); Jayflex L911P (CAS No. 68515-43-5); Jayflex L11P (CAS No. 3648-20-2); Witamol 110 (CAS No. 68515-51-5); Witamol 118 (di-n-C8-C10-alkyl phthalate) (CAS No. 71662-46-9); Unimoll BB (CAS No. 85-68-7); Linplast 1012 BP (CAS No. 90193-92-3); Linplast 13XP (CAS No. 27253-26-5); Linplast 610P (CAS No. 68515-51-5); Linplast 68 FP (CAS No. 68648-93-1); Linplast 812 HP (CAS No. 70693-30-0); Palatinol AH (CAS No. 117-81-7); Palatinol 711 (CAS No. 68515-42-4); Palatinol 911 (CAS No. 68515-43-5); Palatinol 11 (CAS No. 3648-20-2); Palatinol Z (CAS No. 26761-40-0); Palatinol DIPP (CAS No. 84777-06-0); Jayflex 77 (CAS No. 71888-89-6); Palatinol 10 P (CAS No. 53306-54-0); Vestinol AH (CAS No. 117-81-7).

It is pointed out that the core hydrogenation of each isomer used in the core hydrogenation of aromatic polycarboxylic acids or their esters may result in at least two stereoisomeric hydrogenation products. The ratios of the resulting stereoisomers to each other depend on the catalyst used and on the hydrogenation conditions.

All hydrogenation products having any desired ratio(s) of the stereoisomers to each other may be used without separation.

The invention further provides the use of the alicyclic polycarboxylic esters prepared according to the invention as plasticizers in plastics. Preferred plastics include PVC, homo- and copolymers based on ethylene, propylene, butadiene, vinyl acetate, glycidyl acrylate, glycidyl methacrylate, acrylates, acrylates having alkyl radicals of branched or unbranched alcohols having from one to ten carbon atom(s) bonded to the oxygen atom of the ester group, styrene or acrylonitrile, or homo- or copolymers of cyclic olefins.

Examples of representatives of the above groups include the following plastics:

polyacrylates having the same or different alkyl radicals having from 4 to 8 carbon atoms bonded to the oxygen atom of the ester group, in particular having the n-butyl, n-hexyl, n-octyl, 2-ethylhexyl or isononyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers and/or nitrocellulose.

Furthermore, the alicyclic polycarboxylic esters prepared according to the invention may be used for modifying plastic mixtures, for example the mixture of a polyolefin with a polyamide.

Mixtures of plastics and the alicyclic polycarboxylic esters prepared according to the invention likewise form part of the subject matter of the present invention. Suitable plastics are the compounds already mentioned. Such mixtures preferably comprise at least 5% by weight, more preferably 20-80% by weight, most preferably 30-70% by weight, of the alicyclic polycarboxylic esters.

Mixtures of plastics, in particular PVC, which comprise one or more of the alicyclic polycarboxylic esters prepared according to the invention may, for example, be present in the following products or be used for their preparation: casings for electrical equipment, for example kitchen appliances, computer casings, casings and components of phonographic and television equipment, pipes, apparatus, cables, wire sheaths insulating tapes or window profiles, in interior decoration, in vehicle and furniture construction, plastisols, floor coverings, medical products, food packaging, seals, films, composite films, phonographic disks, synthetic leather, toys, packaging containers, adhesive tape films, clothing, coatings and as fibers for fabrics.

In addition to the abovementioned applications the alicyclic polycarboxylic esters prepared according to the invention may also be used as a lubricant component, or as a constituent of cooling liquids and metalworking fluids. They may likewise be used as a component in dyes, paints, inks and adhesives.

The examples which follow are intended to illustrate the invention, without restricting its field of application which can be discerned from the description and the patent claims.

EXAMPLE 1

Preparation of a Titanium Dioxide Support for a Catalyst According to the Invention Commercially obtainable metatitanic acid ($H_2TiO_3$), an aqueous suspension which formally contains 30% by mass of titanium dioxide and 11% by mass of sulfuric acid was filtered with the aid of a filter press. For every 1 kg of suspension used, the filter cake was washed with 5000 g of water. The damp filter cake formally had a content of 41.5% by mass of titanium dioxide and 5.3% by mass of sulfuric acid.

85 g of barium nitrate were added at room temperature to a suspension of 3000 g of filter cake and 3500 g of water in a 10 l stirred tank. The addition of barium nitrate resulted in a portion of the sulfuric acid being converted to barium sulfate. After stirring for one hour at room temperature, the suspension was filtered. The filter cake obtained was dried at 110° C. for five hours and then calcined at 520° C. for 3 hours. In this time, the content of "free sulfate" in the form of sulfur trioxide was further reduced.

The solid obtained formally contained 91.5% by mass of titanium dioxide, 5.5% by mass of barium sulfate and 3.1% by mass of free sulfate. This solid was ground to give two powder types and the desired particle size fraction was sieved out. One powder consisted of particles having particle sizes of from 1 to 30 μm, and the other powder of particles having particle sizes of from 20 to 500 μm. The two different powder types were mixed in a 1/1 ratio. To each 1 kg of powder mixture, 13 g of polyethylene oxide (Polyox WSR 301, manufacturer Union Carbide Corporation), 13 g of methylcellulose (Culminal MPHC 50, manufacturer Aqualon-Hercules GmbH), 70 g of glass fibers (8031, manufacturer Bayer AG), 70 g of ethylene glycol and 200 g of water were added. The resulting mixture was homogenized in a kneader and then shaped with the aid of an extruder into extrudates in the form of a cylinder having a circular diameter of 1.5 mm and a length of from 4 to 6 mm. The extrudates were dried at 80° C. for three hours and then calcined at 450° C. for five hours.

The physical parameters of the support A for the catalyst according to the invention prepared according to example 1 were compiled in table 1. As a comparison, the parameters of a support B frequently used in industry, from which no catalyst according to the invention can be prepared, are listed.

TABLE 1

Properties of the carriers used

| Material | BET surface area in g/m$^2$ to DIN 66131 (N$_2$ adsorption) | Average pore diameter in nm to DIN 66133 (Hg porosimetry) | Total pore volume in ml/g | Proportion of the pore volume of the macropores in % | Proportion of the pore volume of the sum of mesopores and micropores in % | Manufacturer or type designation |
|---|---|---|---|---|---|---|
| A: TiO$_2$ | 75 | 14.8 | 0.33 | <2 | >98 | H 9063 |
| B: α-Al$_2$O$_3$ non-inventive | 7 | 206.5 | 0.64 | >97 | <3 | Axence SP 512 |

The total pore volume was determined from the sum of the pore volumes of the pores having a pore diameter >7.6 nm (determined by Hg porosimetry) and pores having a pore diameter <7.6 nm (determined by the N$_2$ adsorption method).

EXAMPLES 2 AND 3

Preparation of the hydrogenation catalysts A and B For the preparation of hydrogenation catalysts based on the supports detailed in table 1, the supports were first dried at 80° C. After drying, the supports were saturated or spray-dried with an aqueous ruthenium(III) nitrate solution which contained a ruthenium concentration of 0.8% by weight.

For the saturation of the support, the Ru solution in nitric acid was diluted with water to a volume corresponding to the pore volume of the support.

The Ru solution was applied to the support material by dropwise application or preferably by uniform spraying while circulating the support. After drying at 120° C. under nitrogen, the support coated with ruthenium salt was activated (reduced) in a hydrogen/nitrogen mixture, (ratio 1:9) at 200° C. for over 6 hours.

N.B.: The catalysts prepared in this way were referred to in the following text by the same capital letters as the parent supports, and the active metal and its contents were reported in subsequent brackets.

EXAMPLES 3-6

The hydrogenation experiments were carried out according to the following general method:

90.7 g of the catalyst were initially charged in a catalyst basket, cautiously reduced in a 1000 ml pressure reactor in a hydrogen stream according to the above method and then admixed with 590 g of liquid diisononyl phthalate (Vestinol 9, OXENO Olefinchemie GmbH). The DINP was hydrogenated with pure hydrogen. After hydrogenating the starting material, the reactor was decompressed and the reaction mixture was analyzed by means of gas chromatography for its content of the target product diisononyl cyclohexane-1,2-dicarboxylate (DINCH). The conversion of DINP was always above 99.9%.

The experimental conditions of the hydrogenation examples and their results were compiled in table 2:

TABLE 2

DINP hydrogenation/hydrogenation examples

| Hydrogenation examples | Catalyst | Reactant | Pressure in bar | Temperature in ° C. | Reaction time in hours | Content of DINCH in % |
|---|---|---|---|---|---|---|
| 3 | A (1% Ru) | DINP | 200 | 80 | 2.5 | 99.4 |
| 4 | A (1% Ru) | DINP | 200 | 100 | 1 | 99.3 |
| 5 | A (1% Ru) | DINP | 50 | 120 | 0.8 | 99.6 |
| 6 Comparative example | B (1% Ru) | DINP | 200 | 80 | 20 | 99.4 |

It can thus be demonstrated that the type A catalyst according to the invention exhibits a distinctly higher hydrogenation activity than catalyst B.

In the above detailed description, reference was made by way of non-limiting examples to preferred embodiments of the invention. Obviously, numerous modifications and variations of the present invention are possible in light of the above teachings. It is therefore to be understood that within the scope of the appended claims, the invention may be practiced otherwise than as specifically described herein.

The invention claimed is:

1. A process for catalytically hydrogenating at least one of an aromatic polycarboxylic acid compound, an aromatic monocarboxylic acid compound, and derivatives thereof to a corresponding alicyclic compound, comprising:
    hydrogenating the aromatic polycarboxylic and/or monocarboxylic acid compound with a hydrogen-containing gas over a catalyst on or in a support material;
    wherein:
    the catalyst comprises at least one metal of the eighth transition group of the Periodic Table;
    the support material consists of titanium dioxide having a content of from 1.0 to 5.5% by mass of free sulfate or titanium dioxide having a content of from 1.0 to 4.0% by mass of barium;
    the support material has an average pore diameter of from 2 to 50 nm; and
    over 95% of a total pore volume of the support material is accounted for by pores having a diameter of less than 50 nm.

2. The process as claimed in claim 1, wherein a specific surface area of the support material is between 1 and 350 m$^2$/g.

3. The process as claimed in claim 1, wherein the catalyst further comprises at least one metal of the first transition group of the Periodic Table.

4. The process as claimed in claim 1, wherein the catalyst further comprises at least one metal of the seventh transition group of the Periodic Table.

5. The process as claimed in claim 1, wherein the at least one of the aromatic polycarboxylic acid compound, the aromatic monocarboxylic acid compound, and derivatives thereof is selected from the group consisting of a carboxylic acid of benzene, a carboxylic acid of diphenyl, a carboxylic acid of naphthalene, a carboxylic acid of diphenyl oxide, a carboxylic acid of anthracene, and corresponding anhydrides and esters.

6. The process as claimed in claim 5, wherein:
    the at least one of the aromatic polycarboxylic acid compound, the aromatic monocarboxylic acid compound, and derivatives thereof is a carboxylic ester; and
    an alcohol component of the carboxylic ester is selected from the group consisting of a branched or unbranched alkoxyalkyl group having from 1 to 25 carbon atoms, a branched or unbranched cycloalkyl group having from 1 to 25 carbon atoms, and a branched or unbranched alkyl group having from 1 to 25 carbon atoms.

7. A process for catalytically hydrogenating at least one of an aromatic polycarboxylic acid compound, an aromatic monocarboxylic acid compound, and derivatives thereof to a corresponding alicyclic compound, comprising:
    hydrogenating the aromatic polycarboxylic and/or monocarboxylic acid compound with a hydrogen-containing gas over a catalyst on or in a support material;
    wherein:
    the catalyst comprises at least one metal of the eighth transition group of the Periodic Table;
    the support material consists of titanium dioxide having a content of from 1.0 to 5.5% by mass of free sulfate or titanium dioxide having a content of from 1.0 to 4.0% by mass of barium;
    the support material has an average pore diameter of from 2 to 50 nm; and
    over 97% of a total pore volume of the support material is accounted for by pores having a diameter of less than 50 nm.

8. The process as claimed in claim 7, wherein a specific surface area of the support material is between 1 and 350 m$^2$/g.

9. The process as claimed in claim 7, wherein the catalyst further comprises at least one metal of the first transition group of the Periodic Table.

10. The process as claimed in claim 7, wherein the catalyst further comprises at least one metal of the seventh transition group of the Periodic Table.

11. The process as claimed in claim 7, wherein the at least one of the aromatic polycarboxylic acid compound, the aromatic monocarboxylic acid compound, and derivatives thereof is selected from the group consisting of a carboxylic acid of benzene, a carboxylic acid of diphenyl, a carboxylic acid of naphthalene, a carboxylic acid of diphenyl oxide, a carboxylic acid of anthracene, and corresponding anhydrides and esters.

12. The process as claimed in claim 11, wherein:
    the at least one of the aromatic polycarboxylic acid compound, the aromatic monocarboxylic acid compound, and derivatives thereof is a carboxylic ester; and
    an alcohol component of the carboxylic ester is selected from the group consisting of a branched or unbranched alkoxyalkyl group having from 1 to 25 carbon atoms, a branched or unbranched cycloalkyl group having from 1 to 25 carbon atoms, and a branched or unbranched alkyl group having from 1 to 25 carbon atoms.

* * * * *